(12) United States Patent
Melnichuk et al.

(10) Patent No.: US 7,728,182 B2
(45) Date of Patent: Jun. 1, 2010

(54) PROCESS FOR PRODUCING HYDROCARBON DERIVATIVE PRODUCTS FROM FEEDSTOCK CONTAINING HYDROCARBONS

(75) Inventors: Larry Jack Melnichuk, Burlington (CA); Karen (Sue) Venita Kelly, Burlington (CA)

(73) Assignee: Woodland Biofuels Inc., Mississauga, Ontario (CA)

( * ) Notice: Subject to any disclaimer, the term of this patent is extended or adjusted under 35 U.S.C. 154(b) by 1110 days.

(21) Appl. No.: 11/184,078

(22) Filed: Jul. 19, 2005

(65) Prior Publication Data

US 2006/0014841 A1    Jan. 19, 2006

Related U.S. Application Data

(60) Provisional application No. 60/588,889, filed on Jul. 19, 2004.

(51) Int. Cl.
*C07C 27/04*    (2006.01)

(52) U.S. Cl. ..................... 568/884; 568/885

(58) Field of Classification Search .................. None
See application file for complete search history.

(56) References Cited

U.S. PATENT DOCUMENTS

| | | | |
|---|---|---|---|
| 3,972,952 A | 8/1976 | Clark | 260/642 R |
| 4,357,480 A | 11/1982 | Barlow | 568/902 |
| 4,395,495 A | 7/1983 | Cummings | 518/704 |
| 4,454,358 A | 6/1984 | Kummer et al. | 568/885 |
| 4,498,909 A | 2/1985 | Milner | 48/209 |
| 4,747,355 A | 5/1988 | van Berkum | 110/229 |
| 4,766,154 A | 8/1988 | Bonnell | 518/700 |
| 4,823,740 A | 4/1989 | Ohshita | 122/4 D |

(Continued)

FOREIGN PATENT DOCUMENTS

CA    2362687    8/2000

(Continued)

OTHER PUBLICATIONS

Invitation to Pay Additional Fees from the International Search Authority dated Oct. 26, 2007 (International application No. PCT/US2007/008560).

(Continued)

*Primary Examiner*—Karl J Puttlitz
(74) *Attorney, Agent, or Firm*—Sunstein Kann Murphy & Timbers LLP

(57) ABSTRACT

The process for producing a predetermined $C_XH_YO_Z$ product from a primary feedstock containing hydrocarbons and a secondary feedstock is disclosed, wherein X, Y and Z are integers. The process includes the steps of: providing primary feedstock; indirectly heating it generally in the absence of oxygen; cleaning the gas stream produced therefrom by removing $CO_2$ and solids; determining the amount of CO and $H_2$ therein; comparing the percentage of CO and $H_2$ in the cleaned gas stream with the required CO and $H_2$ to produce the predetermined $C_XH_YO_Z$ product; determining the additional of CO and $H_2$ required; determining the secondary feedstock; calculating the amount of CO, $H_2$ and heat produced from the secondary feedstock; partially oxidizing the secondary feedstock to produce heat and a secondary gas stream; combining the CO and $H_2$ from both feedstocks to produce a mixed gas stream; adding a catalyst; and distilling to produce the predetermined $C_XH_YO_Z$ product.

19 Claims, 3 Drawing Sheets

U.S. PATENT DOCUMENTS

| | | | |
|---|---|---|---|
| 4,848,249 A | 7/1989 | LePori | 112/234 |
| 4,929,254 A | 5/1990 | Kooiman | 48/76 |
| 4,954,665 A | 9/1990 | Vidal | 568/902.2 |
| 4,971,599 A | 11/1990 | Cordell | 48/76 |
| 5,059,404 A | 10/1991 | Mansour | 423/201 |
| 5,079,267 A | 1/1992 | Kao | 518/704 |
| 5,120,885 A | 6/1992 | Tsukada | 568/885 |
| 5,138,982 A | 8/1992 | Ohshita | 122/4 D |
| 5,189,203 A | 2/1993 | Hansen | 560/232 |
| 5,218,931 A | 6/1993 | Gorzegno | 122/4 D |
| 5,226,927 A | 7/1993 | Rundstrom | 48/76 |
| 5,233,099 A | 8/1993 | Tabata | 568/885 |
| 5,233,100 A | 8/1993 | Tabata | 568/885 |
| 5,269,262 A | 12/1993 | Salonen | 122/4 D |
| 5,279,234 A | 1/1994 | Bender | 110/210 |
| 5,286,900 A | 2/1994 | Hansen | 560/232 |
| 5,290,327 A | 3/1994 | Rossle | 48/111 |
| 5,334,755 A | 8/1994 | Yoneda | 562/519 |
| 5,344,848 A | 9/1994 | Steinberg | 518/704 |
| 5,414,161 A | 5/1995 | Uhm | 568/885 |
| 5,430,178 A | 7/1995 | Uhm | 560/232 |
| 5,488,143 A | 1/1996 | Uhm | 560/232 |
| 5,573,559 A | 11/1996 | Hilliard | 48/203 |
| 5,580,362 A | 12/1996 | Manulescu | 48/197 R |
| 5,589,599 A | 12/1996 | McMullen | 585/240 |
| 5,599,976 A | 2/1997 | Scates | 562/519 |
| 5,607,487 A | 3/1997 | Taylor | 48/111 |
| 5,620,488 A | 4/1997 | Hirayama | 48/197 R |
| 5,625,094 A | 4/1997 | Nobel | 560/232 |
| 5,663,430 A | 9/1997 | Morris | 562/608 |
| 5,666,890 A | 9/1997 | Craig | 110/229 |
| 5,695,532 A | 12/1997 | Johnson | 48/203 |
| 5,696,284 A | 12/1997 | Baker | 560/232 |
| 5,723,660 A | 3/1998 | Morimoto | 562/519 |
| 5,728,871 A | 3/1998 | Joensen | 562/519 |
| 5,750,007 A | 5/1998 | Clode | 203/3 |
| 5,773,642 A | 6/1998 | Denis | 560/232 |
| 5,840,969 A | 11/1998 | Joensen | 562/519 |
| 5,874,610 A | 2/1999 | Clode | 560/232 |
| 5,877,348 A | 3/1999 | Ditzel | 562/519 |
| 5,883,289 A | 3/1999 | Denis | 560/232 |
| 5,883,295 A | 3/1999 | Sunley | 562/519 |
| 5,900,224 A | 5/1999 | Fujimura | 423/359 |
| 5,900,505 A | 5/1999 | Tustin | 562/519 |
| 5,917,089 A | 6/1999 | Howard | 562/519 |
| 5,922,090 A | 7/1999 | Fujimura | 48/197 R |
| 5,922,092 A | 7/1999 | Taylor | 55/295 |
| 5,932,764 A | 8/1999 | Morris et al. | 562/519 |
| 5,980,858 A | 11/1999 | Fujimura | 423/655 |
| 5,993,751 A | 11/1999 | Moriarty | 422/233 |
| 6,002,054 A | 12/1999 | Ueoka | 568/885 |
| 6,028,119 A | 2/2000 | Kokubu | 518/713 |
| 6,048,374 A | 4/2000 | Green | 48/209 |
| 6,063,355 A | 5/2000 | Fujimura | 423/359 |
| 6,114,279 A | 9/2000 | Fukui | 502/342 |
| 6,127,432 A | 10/2000 | Wegman | 518/715 |
| 6,133,328 A | 10/2000 | Lightner | 518/700 |
| 6,190,429 B1 | 2/2001 | Fujimura | 48/197 R |
| 6,207,865 B1 | 3/2001 | Breitscheidel | 568/705 |
| 6,211,405 B1 | 4/2001 | Cheung | 562/519 |
| 6,283,288 B1 | 9/2001 | Fujinami | 110/346 |
| 6,350,288 B1 | 2/2002 | Hirayama | 48/197 R |
| 6,353,132 B1 | 3/2002 | Zoeller | 562/519 |
| 6,355,595 B1 | 3/2002 | Zoeller | 502/312 |
| 6,355,837 B1 | 3/2002 | Zoeller | 562/519 |
| 6,387,842 B1 | 5/2002 | Wegman | 502/300 |
| 6,395,927 B1 | 5/2002 | Patois | 562/517 |
| 6,455,011 B1 | 9/2002 | Fujimura | 422/139 |
| 6,470,833 B1 | 10/2002 | Hyppanen | 122/4 D |
| 6,486,366 B1 | 11/2002 | Ostgard | 568/863 |
| 6,521,783 B1 | 2/2003 | Wegman | 560/232 |
| 6,596,781 B1 | 7/2003 | Schinski | 518/700 |
| 6,613,111 B2 | 9/2003 | Paisley | 48/89 |
| 6,642,413 B2 | 11/2003 | Thiebaut | 562/517 |
| 6,645,442 B2 | 11/2003 | Kaneko et al. | 422/187 |
| 6,647,903 B2 | 11/2003 | Ellis | 110/348 |
| 6,676,716 B2 | 1/2004 | Fujimura | 48/197 FM |
| 6,680,137 B2 | 1/2004 | Paisley | 429/19 |
| 6,683,224 B1 | 1/2004 | Hourticolon | 568/864 |
| 6,723,886 B2 | 4/2004 | Allison | 568/909 |
| 6,736,955 B2 | 5/2004 | Shaw | 205/450 |
| 6,747,067 B2 * | 6/2004 | Melnichuk et al. | 518/702 |
| 6,779,492 B2 | 8/2004 | Baglione | 122/4 D |
| 6,802,890 B2 | 10/2004 | Hyppanen | 95/271 |
| 6,808,543 B2 | 10/2004 | Paisley | 48/197 R |
| 6,830,597 B1 | 12/2004 | Green | 48/209 |
| 6,837,910 B1 | 1/2005 | Yoshikawa | 48/197 FM |
| 6,846,951 B1 | 1/2005 | Thiebaut | 562/519 |
| 6,863,878 B2 | 3/2005 | Klepper | 423/650 |
| 6,916,951 B2 | 7/2005 | Tustin | 560/231 |
| 6,916,952 B1 | 7/2005 | Le Berre | 560/232 |
| 6,919,488 B2 * | 7/2005 | Melnichuk et al. | 568/840 |
| 6,949,224 B1 | 9/2005 | Miyoshi | 422/139 |
| 6,959,654 B2 | 11/2005 | Abrams | 110/345 |
| 6,972,114 B2 | 12/2005 | Pope | 422/139 |
| 6,991,769 B2 | 1/2006 | Kaneko et al. | 422/187 |
| 6,997,118 B2 | 2/2006 | Chandran | 110/212 |
| 7,008,967 B2 | 3/2006 | Keyser et al. | 518/702 |
| 7,009,070 B2 | 3/2006 | Thiebaut | 560/232 |
| 7,067,558 B2 | 6/2006 | Grobys | 518/700 |
| 7,087,097 B1 | 8/2006 | Karl | 48/76 |
| 7,094,264 B2 | 8/2006 | Steer | 48/198.7 |
| 7,115,774 B2 | 10/2006 | Magna | 562/519 |
| 7,128,004 B2 | 10/2006 | Miyoshi | 110/101 R |
| 7,166,268 B2 | 1/2007 | Fukunaga | 423/651 |
| 7,169,821 B2 | 1/2007 | Branson | 518/702 |
| 2002/0095866 A1 | 7/2002 | Hassett | 48/199 FM |
| 2003/0008928 A1 | 1/2003 | Klepper | 518/704 |
| 2003/0092945 A1 | 5/2003 | Seiki | 568/700 |
| 2003/0115800 A1 | 6/2003 | Yamada et al. | 48/197 |
| 2003/0138365 A1 | 7/2003 | Obidniak et al. | 422/224 |
| 2003/0202912 A1 | 10/2003 | Myohanen | 422/143 |
| 2004/0055216 A1 | 3/2004 | Berger | 48/197 FM |
| 2004/0060236 A1 | 4/2004 | Yoshikawa | 48/63 |
| 2004/0107638 A1 | 6/2004 | Graham | 48/197 |
| 2004/0180971 A1 | 9/2004 | Inoue | 518/702 |
| 2004/0247499 A1 | 12/2004 | Matsuoka | 422/191 |
| 2005/0095183 A1 | 5/2005 | Rehmat | 422/188 |
| 2005/0107482 A1 | 5/2005 | Van Egmond et al. | 518/726 |
| 2005/0112037 A1 | 5/2005 | Darling | 422/139 |
| 2006/0009537 A1 | 1/2006 | Iordache-Cazana | 518/703 |
| 2006/0075946 A1 | 4/2006 | Gounder | 110/346 |
| 2006/0150510 A1 | 7/2006 | Hiltunen | 48/210 |
| 2006/0165589 A1 | 7/2006 | Nielsen | 423/656 |
| 2006/0196398 A1 | 9/2006 | Graham | 110/267 |
| 2007/0010588 A1 | 1/2007 | Pearson | 518/701 |
| 2007/0010589 A1 | 1/2007 | Pearson | 518/702 |
| 2007/0022924 A1 | 2/2007 | Hyppanen | 110/245 |
| 2007/0027220 A1 | 2/2007 | Lattner | 518/726 |

FOREIGN PATENT DOCUMENTS

| | | |
|---|---|---|
| CA | 2456825 | 6/2003 |
| CN | 1477090 | 2/2004 |
| CN | 1563790 | 1/2005 |
| CN | 2745924 Y | 12/2005 |
| CN | 1730611 | 2/2006 |
| CN | 2789258 Y | 6/2006 |
| CN | 2813616 Y | 9/2006 |
| EP | 0 167 300 A1 | 1/1986 |
| EP | 0 335 625 A2 | 10/1989 |
| GB | 2 162 172 A | 1/1986 |
| JP | 2003268390 | 9/2003 |
| JP | 2004051718 | 2/2004 |

| | | |
|---|---|---|
| JP | 2004149556 | 5/2004 |
| JP | 2005112956 | 4/2005 |
| JP | 2005132739 | 5/2005 |
| JP | 2006083293 | 3/2006 |
| JP | 2006131820 | 5/2006 |
| KR | 20010062259 | 7/2001 |
| TW | 292046 Y | 6/2006 |
| WO | WO 03 097847 | 11/2003 |
| WO | WO 2006/021017 | 2/2006 |
| WO | WO 2006/123018 | 11/2006 |
| WO | WO 2006/123146 | 11/2006 |

OTHER PUBLICATIONS

Cambridge Recycling & Energy Systems, Co., *Document*, CareCo, 1994.

D. Dayton, *NREL Presentation*, 4$^{th}$ Annual California Biomass Collaborative Forum, Mar. 27, 2007.

Cambridge Recycling & Energy Systems, Co., *Maverick County Texas Plant*, CareCo, 1980.

Cambridge Recycling & Energy Systems, Co., *Quincy, Florida Gasifier*, CareCo, disclosed 1986.

Cambridge Recycling & Energy Systems, Co., *Process Flow Diagram for Eastman Methanol Reactor*, CareCo, 1980.

Austrian Energy Agency, *Case Study: 2 MWel biomass gasification plant in Güssing* (Austria), Apr. 2004.

David C. Dayton, R&D Needs for Integrated Biorefineries, The 30×30 Vision (30% of 2004 Motor Gasoline Supplied by Biofuels by 2030);Thermochemical Area Leader, National Renewable Energy Laboratory; 4$^{th}$ Annual California Biomass Collaborative Forum, Mar. 27, 2007 (Power Point Presentation).

International Search Report PCT/CA2005/001137 (Jul. 19, 2005).

Database WPI Week 199421 Derwent Publications Ltd., London, GB; AN 1994-174396 XP002475261 & PT 100 794 A (LNETI Lab Nacional Engenharia & Technolog) May 31, 1994 (abstract only).

J. H. Walsh, "The Synthesis of Atmospherically-Neutral Methanol Integrated with the Generation of Electricity in Processes Equipped for the Capture and Sequestering of Carbon Dioxide", *Energy Conversion and Management*, Elsevier Science Publishers, Oxford, GB, 1993, pp. 1031-1049, XPOO2087641 ISSN: 0196-8904.

*The International Preliminary Report on Patentability*, International application No. PCT/US2007/008560, Oct. 28, 2008, 11 pages.

* cited by examiner

PROCESS FOR PRODUCING HYDROCARBON DERIVATIVE PRODUCTS FROM FEEDSTOCK CONTAINING HYDROCARBONS

CROSS REFERENCE TO RELATED PATENT APPLICATION

This patent application relates to U.S. Provisional Patent Application Ser. No. 60/588,889 filed on Jul. 19, 2004 entitled Process for producing ethanol from synthesis gas rich in carbon monoxide.

FIELD OF THE INVENTION

This invention relates to the production of hydrocarbon derivative product and in particular the production of hydrocarbon derivative product from feedstock such as biomass, which may include any from the group of cellulosic plant materials, processed cellulosic products, animal or human excrement, processed animal or human sewage, fossil fuels of any type, plant oils, and other feedstock containing hydrocarbons.

BACKGROUND OF THE INVENTION

A significant challenge of the modern world is to develop a process for dealing with our waste. This is both waste from our manufacturing process and waste from humans such as sewage. Much of this waste is very high in hydrocarbons and accordingly it would be very useful if processes can be developed that capture the energy in this waste to produce products that can have other uses.

For example ethyl alcohol or ethanol, methanol, acetic acid and formaldehyde are but a few liquid organic compounds that are widely used. Specifically ethyl alcohol or ethanol is a widely produced and used chemical. The majority of the market is for 200 proof, or beverage grade, ethanol. The fuel market makes up the next greatest part of the market, and industrial chemical use is the least in demand.

The production of ethanol from the fermentation of cellulosic materials such as grains is well known. The process is not efficient, but is capable of the production of very large quantities at a fairly reasonable cost. The process has the additional advantage of producing the product worldwide and shipping it to other markets as necessary. There are two significant features of the process: one is the need for heat. The fermentation process requires constant temperatures for the biological activity of enzymes and microorganisms to accomplish the conversion. The second feature is the production of carbon dioxide ($CO_2$) from the fermentation itself, but also from the use of fossil fuels to heat the process. The capture of the $CO_2$ is sporadic amongst producers, resulting in an overall significant contribution to the greenhouse gas pool from the industry. The contribution to the pool from the combustion of natural gas or liquid natural gas (LNG) or other fossil fuels is not neutral and is a detriment to the whole process.

The reason for the production of $CO_2$ from fermentation is evident: the molecular structure of cellulose is such that formation of an ethanol molecule leaves molecular fragments. The bacteria have no use for the $CO_2$, as it is a product of their respiration and conversion mechanisms.

U.S. Pat. No. 6,747,067 B2, Process for Converting Cellulosic Material into Liquids, shows forming products using three input streams: 1. gases from the gasification of cellulose; 2. gases from a water/gas shift reaction on the unreacted carbon obtained from the cellulose gasifier; and 3. the gases from combustion of burner gases used to heat the cellulose gasifier.

The gases were blended and formed into chemicals such as acetic acid, formaldehyde or urea formaldehyde, all from methanol. Each step was designed to produced the maximum yield from each gas stream.

Although combining the gas streams has the desired effect of increasing product yields, no planning occurred to deliberately select a second feedstock to add carbon monoxide and hydrogen in a ratio calculated to optimize the yield of product from the primary feedstock. Any residual or unprocessed gases were therefore recycled in the process, as was energy (heat).

Accordingly, it would be advantageous to provide a process for producing ethanol and other $C_XH_YO_Z$ products which involve a tighter control and more efficient use of the oxygen, hydrogen and carbon in any feedstock.

SUMMARY OF THE INVENTION

The present invention is for producing a predetermined $C_XH_YO_Z$ product, wherein X, Y and Z are each an integer, from a primary feedstock supplemented by a secondary feedstock both containing hydrocarbons. The process includes the steps of: providing primary feedstock having a water content of 25% or less; indirectly heating the primary feedstock generally in the absence of oxygen to produce a gas stream and solids; cleaning the gas stream by removing CO2 and solids to produce a cleaned gas stream; determining the amount of CO and $H_2$ in the cleaned gas stream; determining the heat required to indirectly heat the primary feedstock, comparing the percentage of CO and $H_2$ in the cleaned gas stream with the required CO and $H_2$ to produce the predetermined $C_XH_YO_Z$ product; determining the additional of CO and $H_2$ required from the secondary feedstock to provide the correct CO and $H_2$ ratio to form the desired CxHyOz product; determining the secondary feedstock; calculating the amount of CO, H2 and heat produced from the secondary feedstock; partially oxidizing the secondary feedstock to produce heat for the indirect heating of the primary feedstock, and a secondary gas stream; combining the CO and $H_2$ from the cleaned gas stream from the primary feedstock with the gases from the secondary feedstock gas stream to produce a mixed gas stream; adding a catalyst to the mixed gas stream to produce a predetermined $C_XH_YO_Z$ gas; and distilling the predetermined $C_XH_YO_Z$ gas to produce the predetermined $C_XH_YO_Z$ product.

Another aspect of the invention is a process for designing a plant for producing a $C_XH_YO_Z$ product from a primary feedstock containing hydrocarbons and a secondary feedstock. The process includes the steps of: determining the heat required to indirectly heat the primary feedstock; comparing the percentage of CO and $H_2$ in the cleaned gas stream with the required CO and $H_2$ to produce the predetermined $C_XH_YO_Z$ product and determining the additional of CO and $H_2$ required from the secondary feedstock; determining the secondary feedstock; and calculating the amount of CO, $H_2$ and heat to be produced from the secondary feedstock.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
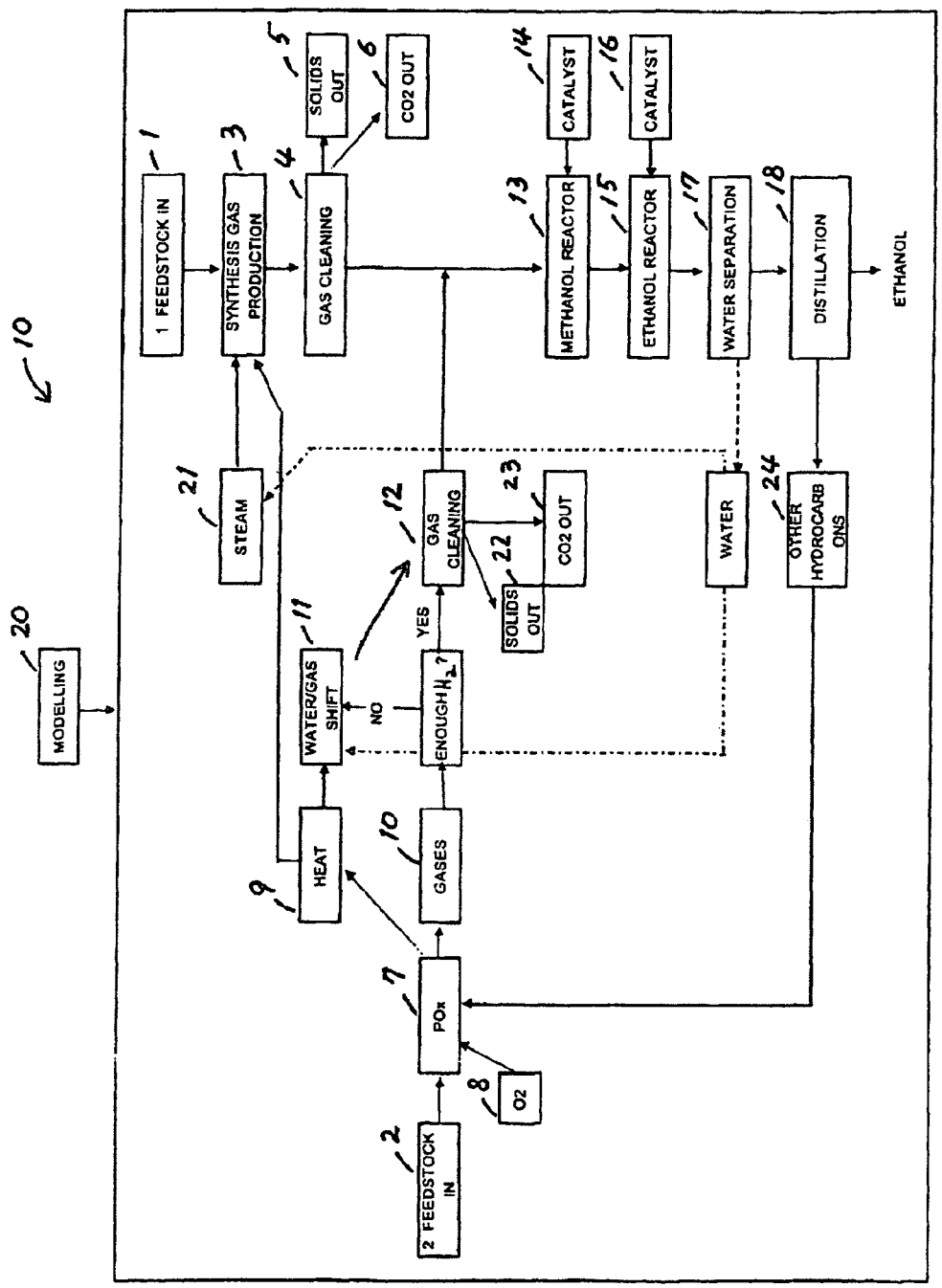
FIG. 1 is a flow diagram of the process of the present invention wherein ethanol is produced.

The process of the present invention describes a method by which the production of CxHyOz, can be optimized by the production of the required mixture of synthesis gas components, wherein X, Y and Z are integers. The CxHyOz products are generally, alcohols, aldehydes, ketones, carboxylic acids, esters and other oxygenated hydrocarbon derivatives. The ratio of the synthesis gas components of carbon monoxide and hydrogen obtained from a primary feedstock can be altered by the addition of a suitable synthesis gas stream from a second feedstock containing additional carbon, hydrogen and oxygen. The resulting mixed syngas stream will contain the specific gas ratios required to form the end product, in this case ethanol, with little or no residual gases to be disposed of. As an example the method of the present invention is described in detail with respect to ethanol ($C_2H_6O$).

A primary synthesis gas stream obtained from the desired feedstock is analyzed for CO and $H_2$ content and compared with the product composition. Depending on the additional components required, a second gas stream is created by partial oxidation or a water-gas shift, or both, of a selected gas, liquid or solid hydrocarbon to form additional synthesis gas. The blended gas stream is then processed using catalysis into methanol, which is further reacted to form ethanol.

There are significant advantages to blending two or more gas streams to produce an end product. 1. With a greater product yield, the whole process becomes more efficient and therefore improves the process economics; 2. The range of feedstocks is broadened, because the primary feedstock does not have to closely match the chemical composition of the output product; 3. The range of products is extended beyond the capabilities of the initial synthesis gas; 4. The need to process or dispose of the unwanted residual gases is greatly reduced. All these advantages have positive economic and environmental benefits.

It is well known that the production of synthesis gas, a mixture of carbon monoxide and hydrogen (syngas), can be achieved through the gasification of hydrocarbon materials such as biomass, natural gas, or petroleum products. The ratios of carbon monoxide to hydrogen produced are determined by the feedstock, the processing method and operating conditions. The resulting syngas is then available for further processing. There are two main uses of syngas; 1) as a chemical feedstock, for example to produce methanol from natural gas, or catalytic reactions such as Fisher-Tropsch (F-T) conversions to make liquid fuels or other hydrocarbons, and 2) as a fuel gas for energy generation.

The majority of synthesis gas produced in the world today for chemical synthesis is from coal or petroleum, with natural gas supplying a small portion. The production of syngas from biomass has become something of a hot topic. New technologies are changing the baseline economics of syngas production, making it an attractive feedstock for chemical synthesis and for the production of super-clean liquid fuels. However, the efficiency of further processing is determined by the quality of the syngas produced, which is a result of the method used. In virtually all cases, unprocessed syngas or unwanted gaseous by-products of the syngas formation remain.

Creation of syngas from biomass can be achieved by steam reforming, pyrolysis or partial oxidation. However, the syngas obtained will always be a ratio of CO:$H_2$ determined by the input material. One feature which is consistent with all processes, regardless of the type or method of the production of synthesis gas from any feedstock, is that the product seldom, if ever, utilizes the syngas components in the exact ratios generated, as in the methanol example below. It is therefore inevitable that the formation of products from the syngas is an inefficient utilization of the feedstock, with excess "leftover" components to be dealt with.

Plant material is composed of cellulose, lignin and trace minerals. The production of syngas from this material typically includes the formation of larger molecules, such as ethane, propane, methane, etc., which further complicate the use of the syngas for further processing, in particular chemical synthesis. This may be reflected in expensive solutions for excess gas disposal or processing which render the formation of the synthesis gas uneconomical, or at best, marginally economical.

The method best suited to provide additional syngas components to an original stream is either the partial oxidation, water-gas shift, or both, of a selected additional material. The material for the reaction is selected based on the end product composition requirement, (the desired end product(s)) and the primary syngas stream composition. This material can be a gas, liquid or solid. Liquids or solids may themselves have to be vaporized or atomized for this step to be successfully achieved.

To illustrate this invention, examples are chosen from the initial gasification of cellulose, the main component of plant material, to produce syngas. The following table illustrates the composition of synthesis gas from processing pure cellulose, $C_6H_{10}O_5$ using the three significant methods available today. Gasification in this instance is defined as the thermal breakdown of material in the absence of oxygen or air. The term 'pyrolysis' or 'destructive distillation' is sometimes used to describe this technique, and in this instance these terms can be used interchangeably in the examples below.

| Technology utilized | Reaction | Syngas composition |
| --- | --- | --- |
| Gasification | $C_6H_{10}O_5$ | $5CO + 5H_2$ |
| steam reforming | $C_6H_{10}O_5 + H_2O$ | $6CO + 6H_2$ |
| partial oxidation | $C_6H_{10}O_5 + \frac{1}{2}O_2$ | $6CO + 5H_2$ |

Note: This table and subsequent ones demonstrate complete reactions, which is the ideal and occurs in theory only. In the real world, these process would also produce $CO_2$, $CH_4$ other small chain hydrocarbons. For clarity, those extraneous reactions are omitted. Also, in the real world, plants are composed also of a substance generally known as lignin, in varying proportions, plus various minerals. Lignin is the term applied to a group of chemicals called polylignols, which have minor variations in composition. Lignin cannot be described by a fixed chemical formula, and is composed of C—H—O, sometimes with sulphur. Because of their complex nature, they are omitted from this illustrative example.

The subsequent utilization of the syngas to form products is limited by the ratio of the components, and has molecular "leftovers" which do not contribute to the product yield.

For example if the desired end product is methanol, $CH_3OH$, the syngas from the table above is subjected to heat, pressure and a catalyst, to form methanol as follows:

| Process | Reaction to form methanol |
|---|---|
| Gasification | $5CO + 5H_2 \rightarrow 2\ CH_3OH + 3CO + H_2$ |
| steam reforming | $6CO + 6H_2 \rightarrow 3\ CH_3OH + 3CO$ |
| partial oxidation | $6CO + 5H_2 \rightarrow 2\ CH_3OH + CO + H_2$ |

The remaining gases of $CO+H_2$ must then be either vented, or further processed. The methanol yield is not affected.

Now, to illustrate the use of the remaining gases, consideration is given to the use of landfill gas to provide further syngas for the reaction to produce additional methanol and reduce the leftover gases.

First, the landfill gas is processed to produce synthesis gas, as follows. Landfill gas is assumed to be composed of one half CH4 and one half $CO_2$.

| Input for syngas supplement | Process | Reaction | Product |
|---|---|---|---|
| Landfill gas | partial oxidation | $CH_4 + CO_2 + \frac{1}{2} O_2$ | $CO + 2H_2 + CO_2$ |
| Landfill gas | water-gas shift | $CH_4 + CO_2 + H_2O$ | $CO + 3H_2 + CO_2$ |

The combination of the partial oxidation gases and the methanol "leftovers" are:

| Process | Remaining gases from MeOH production | $2^{nd}$ syngas from landfill gas (ignoring the $CO_2$) | New gas mixture | Products Methanol + |
|---|---|---|---|---|
| Gasification | $3CO + H_2$ | $CO + 2H_2$ | $4CO + 3H_2$ | $CH_3OH + 3CO + H_2$ |
| steam reforming | $3CO$ | $CO + 2H_2$ | $4CO + 2H_2$ | $CH_3OH + 3CO$ |
| partial oxidation | $CO + H_2$ | $CO + H_2$ | $2CO + 3H_2$ | $CH_3OH + CO + H_2$ |

The combination of the water-gas shift gases and the methanol "leftovers" are:

| Process | Remaining gases from MeOH production | $2^{nd}$ syngas from landfill gas (ignoring the $CO_2$) | New gas mixture | Products Methanol + |
|---|---|---|---|---|
| Gasification | $3CO + H_2$ | $CO + 3H_2$ | $4CO + 4H_2$ | $2\ CH_3OH + 2CO$ |
| steam reforming | $3CO$ | $CO + 3H_2$ | $4CO + 3H_2$ | $CH_3OH + 3CO + H_2$ |
| partial oxidation | $CO + H_2$ | $CO + 3H_2$ | $2CO + 4H_2$ | $2\ CH_3OH$ |

Comparison of Results

The following table illustrates the improvements in yields and reduction in extraneous gases from the processing of cellulose in the above examples.

Numbers in the table refer to the molecules of the indicated component:

| | Products of $1^0$ Syngas | | | Products of landfill gas processing Added to $CO + H_2$ from $1^o$ | | | | | |
|---|---|---|---|---|---|---|---|---|---|
| | | | | Partial oxidation | | | Water-gas Shift | | |
| Process | Methanol | CO | $H_2$ | Methanol | CO | $H_2$ | Methanol | CO | $H_2$ |
| Gasification | 2 | 3 | 1 | 1 | 3 | 1 | 2 | 2 | 0 |
| steam reforming | 3 | 3 | 0 | 1 | 3 | 0 | 1 | 3 | 1 |
| partial oxidation | 2 | 1 | 1 | 1 | 1 | 1 | 2 | 0 | 0 |

| | | Effects of Adding Syngas Streams | | |
|---|---|---|---|---|
| | | Gasification | Steam RF | Partial Oxidtn |
| MeOH | With 2nd stream - pOx | ▲ 150% | ▲ 133% | ▲ 150% |
| CO | With 2nd stream - pOx | No change | No change | No change |
| $H_2$ | With 2nd stream - pOx | No change | No change | No change |
| MeOH | with 2nd stream - W/G | ▲ 200% | ▲ 133% | ▲ 200% |
| CO | with 2nd stream - W/G | ▼ 167% | No change | ▼ 100% |
| $H_2$ | with 2nd stream - W/G | ▼ 100% | ▲ 100% | ▼ 100% |

Interpretation:

In the cases of either partially-oxidizing or water-gas shifting landfill gas, the methanol yield increased, ranging from 133% to 200%. The residual amount of carbon monoxide generally decreased or did not change. The residual amount of $H_2$ either did not change, or generally went down.

This technique for evaluating the yields of methanol and of the by-products is a simplified representation of the process described in this invention. It will also be appreciated that blending the gases in different volumes will also allow more recombinations to take place, so the actual residual gases will not be in the same quantities described in this example. It is obvious that not all real world situations are this simple. Biomass is a more complex substance than the simple cellulose used in the example above, and the ratios of lignin and trace elements vary with each plant species. A biomass-based syngas can therefore vary, and the purpose of this invention is to describe how these variations can be accommodated to render the process efficient. Anyone skilled in the art could obtain the necessary information about the syngas produced from a chosen feedstock, using a specified process. With this knowledge in hand, one skilled in the art could then select the secondary syngas source, and choose either partial oxidation or the water-gas shift reaction, or both, to provide additional syngas. Together, the two syngas streams will produce the highest possible yield, and the lowest possible extraneous components for disposal.

Computer software is available to perform the necessary process design calculations so the process and equipment can be designed to provide maximum yield for the selected feedstock. Computer modeling software requires input of chemical composition of the feedstock, which is the starting point for any process design. Using that information, and utilizing the software libraries to insert the correct equipment specifications, a system can be "built" and operated in real time. A good software program will produce mass and energy balances for the entire system, and can therefore allow iterative changes. It is use of this type of computer software design which sets this invention apart, because it is the basis on which the design of the process is built.

Once constructed, the operating plant gas streams can be monitored with on-line sampling equipment to ensure consistent synthesis gas production occurs according to design. Sampling ports can be built into the system to enable testing at every important stage of the series of events taking place within the process, allowing tight control by the integrated process control system. The plant so designed will not only be more efficient at the design phase, but into the operating phase as well.

Process Description

It will be appreciated that the equipment used to accomplish the goals of the process of the present invention are selected according to the situation at hand.

In FIG. 1, the computer modeling process 20 begins with an analysis of the primary feedstock, which is the feedstock for which the process will be designed. Typically this would be waste biomass such as crop residues, wood residues from harvesting, milling or municipal activities, pulp and paper bark or sawdust, to name a few cellulosic sources. The feedstock could also be organic material such as human or animal sewage, or high protein residues from fermentation of grains often referred to as dry distiller's grains or dry distiller's grains and solubles. Chemical analysis and a metal analysis (such as ICAP) are necessary, to obtain information on carbon, hydrogen, oxygen and nitrogen content, BTU value, water content. and metals present.

To begin with, it is assumed that it is known what the basic process steps will be. In this invention, the steps are: gasification of the primary feedstock to produce a synthesis gas, gas cleaning, blending the gas stream with another cleaned gas stream produced by the partial oxidation of a secondary feedstock, which may or may not have been subjected to a water/gas shift to adjust the carbon monoxide content, then reacting the combined synthesis gases to produce methanol first, then converting the methanol to ethanol.

The process design is thus begun, using computer software. In the model, the feedstock is gasified using indirect heat in the absence of oxygen/air, to produce a primary synthesis gas of carbon monoxide and hydrogen. Also present in the gases will be particulate matter (carbon, or ash) and carbon dioxide. There may also be other hydrocarbon gases such as methane (CH4). The information of the breakdown of the feedstock is derived from experience and literature, and provides the basis for the mass balance of the process. Because other products of gasification are likely to be produced, values for carbon dioxide, methane and small hydrocarbons such as propane and ethane are also fed into the computer simulation model.

The modeling process is iterative. As each step in the input and processing are achieved, the information from the model is evaluated. Adjustments to the volumes of input are made in the model, as are variants in energy supplied for the gasification, volume and temperature of the steam supplied, and gas velocities through the process.

The desired product, in this case ethanol, is then selected. Currently, other products which can alternatively be made are derivatives of methanol, and include formaldehyde (CHOH) and acetic acid (CH3COOH). The carbon monoxide and hydrogen ratio obtained from the gasification of the primary feedstock are measured in the present invention against the ideal amounts of carbon, oxygen and hydrogen needed to form ethanol. A secondary feedstock is then contemplated, in consideration of its carbon content, BTU value, availability and cost. It is selected on the basis of the following questions:

1. How much heat is needed to achieve the gasification of the primary feedstock?
2. How much additional carbon monoxide and hydrogen are required to supplement the primary synthesis gas?
3. Can the gases be obtained from partial oxidation of the secondary feedstock?
4. Will the gas mixture then require further processing by a water/gas shift?

The selection of the secondary feedstock could be a gas, liquid or solid hydrocarbon. Examples of gases include natural gas, landfill gas, propane or butane; examples of liquids include gasoline, diesel fuel, bio-diesel (defined as diesel fuel make from biomass), bio-oil (defined as plant oils produced by reprocessing or from the pyrolysis of wood); examples of solids include wood or any type, crop residues, organic wastes, paper waste, plastics. Once a material is selected, information on the gases which are produced from its partial oxidation are input into the computer model. From evaluation of the gas composition after oxidation, a decision is made to further process the gases using a water/gas shift. The process of the present invention converts carbon monoxide to carbon dioxide, thereby adjusting the final carbon monoxide ratio, a step which may not always be necessary. The gases are then combined with the primary gas stream, and the model can then determine the output of methanol firstly, and then the final ethanol output.

The nature of the computer software allows changes to any input, which are then adjusted manually until the process flow is satisfactory. That typically means that as much ethanol is produced from the inputs as possible, as little carbon monoxide is exhausted from the process, and as little volume of unwanted hydrocarbons from the catalytic steps are recycled into the initial gasification or secondary partial oxidation steps.

During the description of the process steps below, reference will be made to the modeling process. It will become clearer to the reader how the modeling interfaces with the final process design and how changes in feedstock and products can be made to utilize many different feedstocks and produce other methanol derivatives. It will also become obvious to those skilled in the art that methanol may not be produced at all, but another chemical using a different catalyst(s).

The physical process is described as follows:

In FIG. 1, generally at 10, the primary feedstock 1 is prepared by whatever means necessary, such as chipping, grinding, chopping and drying to achieve a moisture content of typically 25%, and a size of 2" or less in any direction. The feedstock is fed into the indirectly-heated gasifier 3 in the absence of air or oxygen, and gasified using steam 21 as a fluidizing medium. The gas stream evolved is cleaned 4 and solids 5 and carbon dioxide 6 removed. The solids may consist of ash or minerals such as sodium, nitrogen compounds, potassium, copper, silica, phosphorus. The exact mixture is of course determined by the composition of the primary feedstock. The carbon dioxide is typically scrubbed out of the gas stream using an amine separator, but other state of the art methods are available. The economics of the process will determine which method is utilized.

A secondary feedstock 2 is prepared by whatever means necessary, such as chipping, grinding, chopping and drying to achieve a moisture content of not more than 25%, and a size of 2" in any direction. The feedstock is then partially oxidized in a gasifier 7 using oxygen 8 which can be supplied from an oxygen generator or molecular sieve. In the event the secondary feedstock is a liquid or a gas, the feedstock can be fed into a burner and partially oxidized, using oxygen 8, supplied from either source. The heat produced from this step is used to heat the gasifier 3 to gasify the primary feedstock, and, if required, the water/gas shift reactor 11. The gases produced from the partial oxidation process are either cleaned 12 or sent to the water/gas shift reactor 11. Gases emerging from the water/gas shift reactor 11 are cleaned 12 and solids 22 and carbon dioxide 23 removed. The solids are again determined by the chemical composition of the secondary feedstock, but will be low volume if a gas or liquid is utilized. The carbon dioxide is scrubbed out using whatever method is most economical, as with the cleaning of gases in the primary step.

Gases from the cleaning process 12 are merged with the primary gases emerging from the gas cleaning sequence 4. The merged gas stream is sent to the methanol reactor 13 which is supplied with catalyst 14. The catalyst is nickel and copper generally in the proportions of 93:7, and are known to those skilled in the art. The product methanol and any other hydrocarbons formed in the reactor 13 are sent to the ethanol reaction process 15. The catalyst 16 is used to convert the methanol to ethanol and is generally a nickel copper catalyst in the proportions of 75:25, also known to those skilled in the art. The process may be reactive distillation, in which the methanol is converted to methyl acetate, then split into ethanol and methanol. In this case, the methanol is continuously recycled through to be reprocessed.

This catalytic sequence from synthesis gas to ethanol utilizes known catalysts and techniques. However, catalysts are always under development. We found that the described sequence is the most efficient to date, with high catalyst selectivity and conversion. In the future, other catalysts may be developed to go directly from synthesis gas to ethanol in one step, in which case that would be the method of choice in the process of the present invention. In the future, new catalysts may also be developed to produce other chemicals directly from synthesis gas. As time goes by, the process of the present invention can be adapted to utilize those catalysts, broadening the selection of products available from biomass or other primary feedstock.

The products of the ethanol reaction step 15 are sent to a water separator 17 and the water is recycled into the system for use in the water/gas shift reactor 11 or the steam generator 21 to supply steam for the gasifier. The products are then sent to distillation 18, in which the ethanol is purified. Any other hydrocarbon liquids 24 removed in the distillation are sent to the partial oxidation process 7 or to the primary gasifier 3.

Figure 2:
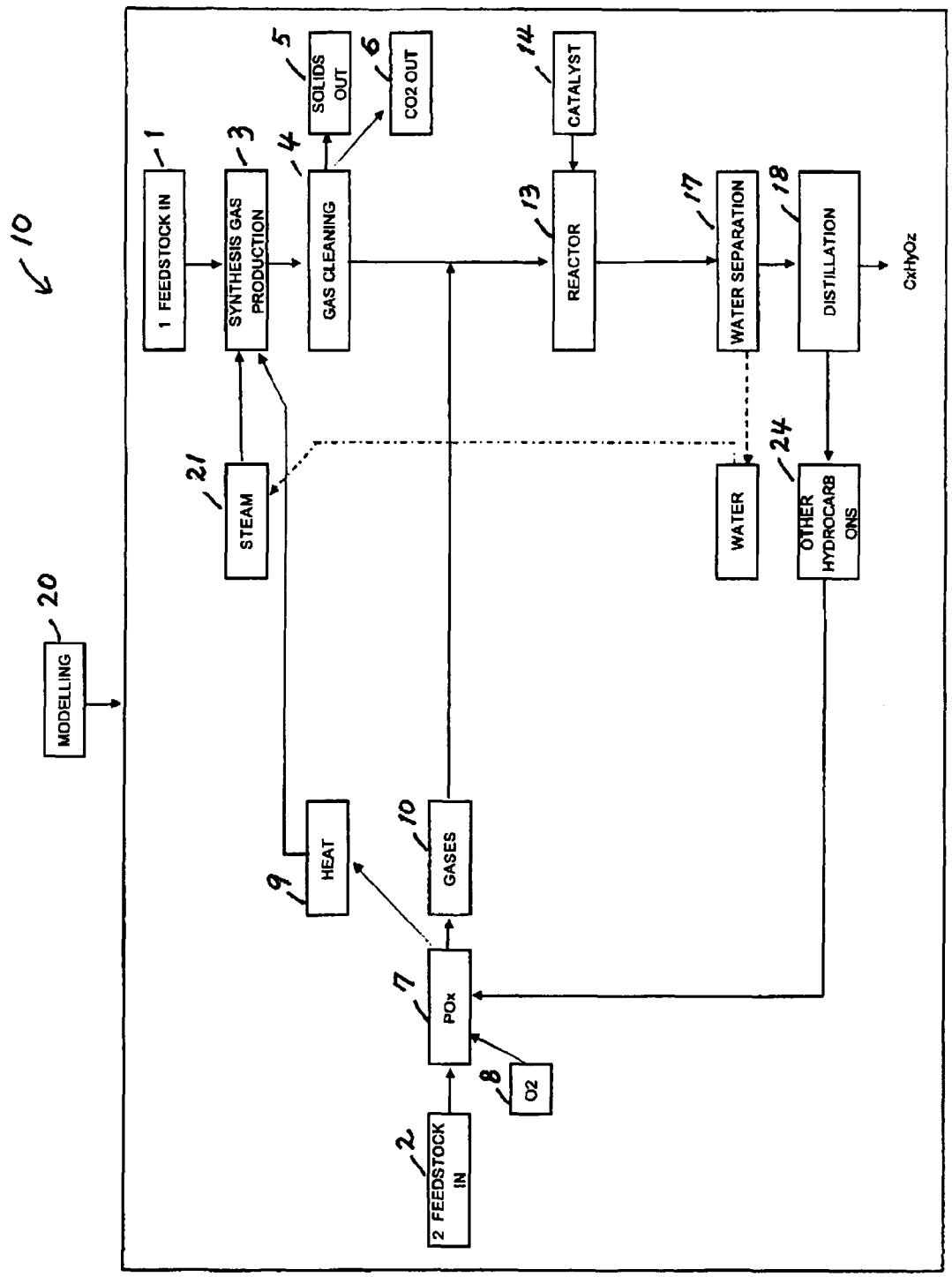
FIG. 2 is a flow diagram of the process of the present invention showing the production of a general $C_XH_YO_Z$ product.
Figure 3:
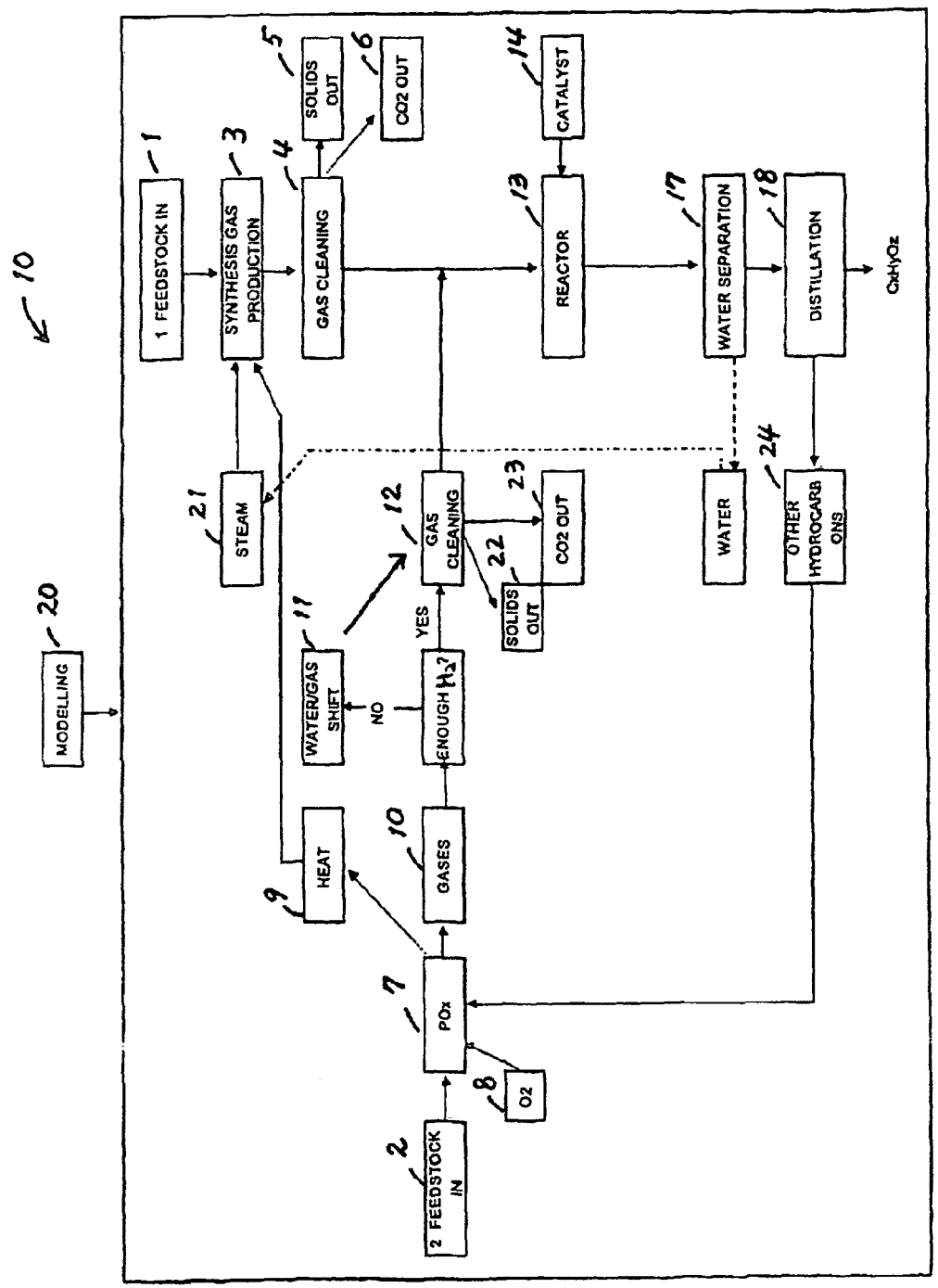
FIG. 3 is a flow diagram similar to that shown in FIG. 2 but including further processing steps in regard to the secondary feedstock.

It will be appreciated by those skilled in the art that the above description is in regard to a specific example of the invention of the present invention. The invention can be described in more general terms and these are shown in FIGS. 2 and 3. Specifically in FIG. 2 the example is for the instance where the secondary feed stock 2 is a predetermined gas such that certain steps would not be required. Specifically the water/gas shift step and the gas cleaning step would not be required. Further, as discussed above with the advent of new catalyst it may be possible to go directly to the desired $C_XH_YO_Z$ product without going through methanol. Similarly FIG. 3 is similar to both FIGS. 1 and 2 in that it includes the water/gas shift and the gas cleaning steps of FIG. 1 but it contemplates other catalyst than FIG. 2.

It will be recognized by those skilled in the art that the range $C_XH_YO_Z$ products which can be formed from synthesis gas are limited only by the availability of catalysts to do so. Certain ones have been available for many years, such as the Fischer-Tropsch group, which are used heavily to produce fuels and chemicals from the synthesis gas generated from the gasification of coal. There are many other catalysts designed to perform specific reactions such as the conversion synthesis gas to methanol. The challenge is to fit the catalyst to the desired product with the most effective use of the synthesis gas produced.

Hydrocarbons (compounds of carbon and hydrogen) are of prime economic importance because they encompass the constituents of the major fossil fuels (coal, petroleum, natural gas, etc.) and biofuels, as well as plastics, waxes, solvents and oils. Oxygenated hydrocarbons include alcohols, ketones, aldehydes, and carboxylic acids. These are also very important as fuels and as building blocks for pharmaceuticals, industrial chemicals, and man-made materials.

As used herein, the terms "comprises" and "comprising" are to be construed as being inclusive and opened rather than exclusive. Specifically, when used in this specification including the claims, the terms "comprises" and "comprising" and variations thereof mean that the specified features, steps or components are included. The terms are not to be interpreted to exclude the presence of other features, steps or components.

It will be appreciated that the above description related to the invention by way of example only. Many variations on the invention will be obvious to those skilled in the art and such obvious variations are within the scope of the invention as described herein whether or not expressly described.

What is claimed as the invention is:

1. A process for producing an ethanol product from a primary feedstock containing hydrocarbons comprising the steps of:
    subjecting the primary feedstock with a water content of not greater than 25% to indirect heating, substantially in the absence of oxygen, by a secondary feedstock to create a primary synthesis gas stream comprising CO and $H_2$ and solids;
    cleaning the gas stream by removing $CO_2$ and solids to produce a cleaned gas stream;
    determining the amount of CO and $H_2$ in the cleaned gas stream;
    comparing the percentage of CO and $H_2$ in the cleaned gas stream with the required CO and $H_2$ ratio to form the ethanol product;
    calculating the amount of the secondary feedstock required for indirect heating of the primary feedstock;
    depending on additional components required to produce the ethanol product, determining an additional quantity of CO and $H_2$ which may be required as a secondary gas stream from the secondary feedstock;
    partially oxidizing the calculated amount of secondary feedstock to produce heat required for the indirect heating of the primary feedstock;
    combining the determined additional quantity of CO and $H_2$ which may be required from the secondary gas stream with the cleaned gas stream to produce a mixed gas stream;
    adding a catalyst to the mixed cleaned gas stream and reacting the CO and $H_2$ with the catalyst in a methanol reactor to produce methanol;
    converting the methanol into methyl acetate;
    converting the methyl acetate into ethanol and methanol; and
    distilling the ethanol and methanol to produce the ethanol product.

2. A process as claimed in claim 1 further including the steps of determining whether the quantity of $H_2$ in the secondary gas stream meets the additional quantity of $H_2$ required for the ethanol product, and if the quantity of $H_2$ is not enough, passing CO through a water/gas shift wherein the CO is mixed with water to produce $H_2$ and $CO_2$ and adding $H_2$ so obtained and then passing the remaining CO and $H_2$ to the combining step.

3. A process as claimed in claim 2 further including the step of cleaning the secondary gas stream and removing $CO_2$ and solids to produce a cleaned secondary gas stream.

4. A process as claimed in claim 3 wherein steam is used for the indirect heating step.

5. A process as claimed in claim 3 wherein a raw primary feedstock has a water content of higher than 25% and further including the step of drying the raw primary feedstock to produce the primary feedstock.

6. A process as claimed in claim 3 wherein the $CO_2$ is removed using an amine separator.

7. A process as claimed in claim 3 wherein the catalyst is a nickel and copper catalyst.

8. A process as claimed in claim 3 further comprising recycling the methanol.

9. A process as claimed in claim 8 further comprising purifying the ethanol.

10. A process as claimed in claim 3 wherein the primary feedstock is chosen from a group consisting of waste biomass and organic material.

11. A process as claimed in claim 10 wherein the waste biomass is chosen from a group consisting of crop residues, wood residues from harvesting, milling and municipal activities, pulp and paper bar and sawdust.

12. A process as claimed in claim 10 wherein the organic material is chosen from a group consisting of human and animal sewage, and high protein residues from the fermentation of alcohols from grains, called dry distiller's grains or dry distiller's grains and solubles.

13. A process as claimed in claim 3 wherein the secondary feedstock is chosen from a group consisting of hydrocarbon fuels in gas, liquid and solid form, biomass containing cellulose and organic material.

14. A process as claimed in claim 1 wherein the primary feedstock is chosen from the group consisting of waste biomass and organic material.

15. A process as claimed in claim 14 wherein the waste biomass is chosen from a group consisting of crop residues, wood residues from harvesting, milling and municipal activities, pulp and paper bar and sawdust.

16. A process as claimed in claim 14 wherein the organic material is chosen from a group consisting of human and animal sewage, and high protein residues from the fermentation of alcohols from grains, called dry distiller's grains or dry distiller's grains and solubles.

17. A process as claimed in claim 1 wherein the secondary feedstock is chosen from the group consisting of hydrocarbon fuels in gas, liquid and solid form, biomass containing cellulose and organic material.

18. A process as claimed in claim 1 wherein steam is used for the indirect heating step.

19. A process as claimed in claim 1 wherein a raw primary feedstock has a water content of higher than 25% and further including the step of drying the raw primary feedstock to produce the primary feedstock.

* * * * *